United States Patent [19]

Rizkalla

[11] Patent Number: 4,482,497

[45] Date of Patent: Nov. 13, 1984

[54] PREPARATION OF CARBOXYLIC ACIDS

[75] Inventor: Nabil Rizkalla, River Vale, N.J.

[73] Assignee: The Halcon SD Group, Inc., New York, N.Y.

[21] Appl. No.: 430,094

[22] Filed: Sep. 30, 1982

[51] Int. Cl.$^3$ .............................................. C07C 51/12
[52] U.S. Cl. .............................. 260/413; 260/410.9 R; 260/549; 560/105; 560/109; 560/114; 560/232; 562/406; 562/497; 562/517; 562/519
[58] Field of Search ............... 562/519, 406, 497, 517; 260/413; 560/232, 204, 114

[56] References Cited

U.S. PATENT DOCUMENTS 2,650,245 8/1953 Thomas et al. ..................... 562/519
4,133,963 1/1979 Holmes .............................. 562/519

FOREIGN PATENT DOCUMENTS 2749955 5/1978 Fed. Rep. of Germany ...... 562/519

Primary Examiner—Vivian Garner
Attorney, Agent, or Firm—William C. Long; Riggs T. Stewart; Harold N. Wells

[57] ABSTRACT

A carboxylic acid, such as acetic acid, is prepared by carbonylation of a hydrocarbyl alcohol, such as methanol by the use of a molybdenum-nickel-alkali metal or a tungsten-nickel-alkali metal co-catalyst in the presence of an iodide or bromide.

4 Claims, No Drawings

PREPARATION OF CARBOXYLIC ACIDS

This invention relates to the preparation of carboxylic acids, more particularly mono-carboxylic acids, and especially lower alkanoic acids, such as acetic acid, by carbonylation.

Acetic acid has been known as an industrial chemical for many years and large amounts are used in the manufacture of various products. Proposals for producing carboxylic acids by the action of carbon monoxide upon alcohols (carbonylation) have been described, for example, in Reppe et al. U.S. Pat No. 2,729,651 and in Holmes U.S. Pat. Nos. 4,133,963 and 4,218,340. However, such prior proposals involving carbonylation reactions have required the use of very high pressures. Carbonylation processes effective at lower pressures have also been proposed. French Pat. No. 1,573,130, for example, describes the carbonylation of methanol and mixtures of methanol with methyl acetate in the presence of compounds of Group VIII noble metals such as iridium, platinum, palladium, osmium and ruthenium and in the presence of bromine or iodine under more moderate pressures than those contemplated by Reppe et al. and Holmes. U.S. Pat. Nos. 3,769,329 and 3,772,380 produce acetic acid from the same reactants using an iridium or rhodium component with bromine or iodine. Schultz (U.S. Pat. Nos. 3,689,533 and 3,717,670) has disclosed a vapor-phase process for acetic acid production employing various catalysts comprising a rhodium component dispersed on a carrier. These lower-pressure carbonylation disclosures, however, require the use of expensive noble metals. More recently, Belgian Pat. No. 860,557 has proposed the preparation of carboxylic acids by carbonylation of alcohols in the presence of a nickel catalyst promoted by a trivalent phosphorus compound and in the presence of an iodide. Belgian Pat. No. 891,609 discloses a related process for the carbonylation of alcohols to produce carboxylic acids which uses a molybdenum-nickel or tungsten-nickel co-catalyst in the presence of a promoter comprising an organo-phosphorus or an organo-nitrogen compound. European published application No. 0 035 458 shows the carbonylation of alcohols to carboxylic acids in the presence of a nickel catalyst and an alkyl or acyl halide in the presence of an alkaline salt and in the presence of an initially charged carboxylic acid. European published application No. 0 018 927 shows a related process using a nickel catalyst and an alkali or alkaline earth halide which is characterized by the use of a solvent which is a tetramethylenesulfone or its derivative or an alkyl ether of a polyethylene glycol or an amide. While these processes involving nickel catalysts make possible carbonylation at modest pressures without the use of a noble metals, there is room for improved reaction rate and productivity without need for organic promoters.

It is accordingly an object of the present invention to provide an improved process for the manufacture of carboxylic acids, especially lower alkanoic acids, such as acetic acid, which requires neither high pressures nor Group VIII noble metals and makes possible the production of carboxylic acids in high yields in short reaction times without need for organic promoters.

In accordance with the invention, carbonylation of a hydrocarbyl alcohol is carried out by using a molybdenum-nickel-alkali metal or a tungsten-nickel-alkali metal co-catalyst and in the presence of an iodide. The surprising discovery has been made that this co-catalyst system in an environment of the character indicated makes possible carbonylation of alcohols not only at relatively low pressures but with rapid, high yield production of carboxylic acids. The iodide can be replaced with a bromide.

The outstanding effectiveness of the catalyst system of the process of this invention is particularly surprising in view of the experimental data reported in European published application No. 0 035 458 in which experiments using nickel in combination with molybdenum or tungsten showed absolutely no reaction even after two hours. It has also been observed that when nickel-based catalysts are ordinarily used in carbonylation reactions, there is a tendency for the nickel components to be volatilized and to appear in the vapors from the reaction. It has been surprisingly found that, with the catalyst system of this invention, the volatility of the nickel is strongly suppressed and a highly-stable catalyst combination results.

Thus, in accordance with the invention, carbon monoxide is reacted with a hydrocarbyl alcohol such as a lower alkyl alcohol, to produce a carboxylic acid, such as a lower alkanoic acid, the carbonylation taking place in the presence of an iodide, e.g., a hydrocarbyl iodide, especially a lower alkyl iodide, such as methyl iodide, and in the presence of the co-catalyst combination which has been identified above. Acetic acid, for example, can be effectively prepared in a representative case by subjecting methyl alcohol to carbonylation. While it is preferred to charge the alcohol directly to the reaction, alcohol precursors such as esters, e.g., methyl acetate, or ethers, e.g., dimethyl ether, can be used in combination with equivalent amounts of water. Reference to alcohols, therefore, includes such precursors.

In like manner, other lower alkanoic acids, such as propionic acid, butyric acid, and valeric acid, can be produced by carbonylating the corresponding lower alkyl alcohol such as ethyl alcohol, propyl alcohol, and the like. Similarly, other alkanoic acids, such as those containing up to 12 carbons, for example capric acid, caprylic acid, and lauric acid, and like higher carboxylic acids are produced by carbonylating the corresponding alcohol, e.g., alkyl alcohols containing up to 11 carbon atoms in the alkyl group, heptyl alcohol, nonyl alcohol, undecyl alcohol, phenol, and the like.

The above-described reaction can be expressed as follows:

$$CO + ROH \rightarrow RCOOH \qquad (1)$$

wherein R is a hydrocarbyl radical which may be saturated, e.g., alkyl of 1 to 11 carbon atoms, or monocyclic aryl, e.g., phenyl or aralkyl, e.g., benzyl. Preferably, R is lower alkyl, i.e., an alkyl group of 1 to 4 carbon atoms, such as methyl, ethyl, n-propyl, i-propyl, n-butyl, sec-butyl, and t-butyl. The hydrocarbyl radical may be substituted with substituents which are inert in the reactions of the invention.

The more volatile components such as alkyl iodide and unreacted alcohol and by-products such as esters and ethers in the final product mixture can be readily removed, as by distillation, for recycling, and the net yield of product is substantially exclusively the desired carboxylic acid. In the case of liquidphase reaction, which is preferred, the organic compounds are easily separated from the metal-containing components, as by distillation. The reaction is suitably carried out in a reaction zone to which the carbon monoxide, the alcohol, the iodide, and the co-catalyst are fed.

In employing the process of the invention, temperatures over a-wide range, e.g., 150° C. to 250° C., are suitable but temperatures greater than 180° C. up to 250° C. are preferred, and the more preferred temperatures generally lie in the range of 200° to 225° C. Temperatures lower than those mentioned can be used but they tend to lead to reduced reaction rates, and higher temperatures may also be employed but there is no particular advantage in their use. The time of reaction is also not a parameter of the process and depends largely upon the temperature employed, but typical residence times, by way of example, will generally fall in the range of 0.1 to 20 hours. The reaction is carried out under superatmospheric pressure but, as previously mentioned, it is a feature of the invention that excessively high pressures, which require special high-pressure equipment, are not necessary. In general, the reaction is effectively carried out by employing a carbon monoxide partial pressure which is preferably at least 15 but less than 2,000 psi, most preferably 15 to 500 psi and particularly 30 to 200 psi, although CO partial pressures of 1 to 5,000 or even up to 10,000 psi can also be employed. By establishing the partial pressure of carbon monoxide at the values specified, adequate amounts of this reactant are always present. The total pressure is, of course, that which will provide the desired carbon monoxide partial pressure and preferably it is that required to maintain the liquid phase and in this case the reaction can be advantageously carried out in an autoclave or similar apparatus. The final reaction mixture will normally contain volatile components such as hydrocarbyl iodide, unreacted alcohol and may contain the corresponding ester and/or ether along with the product acid and these volatile components, after separation from the acid, can be recycled to the reaction. At the end of the desired residence time the reaction mixure is separated into its several constituents, as by distillation. Preferably, the reaction product is introduced into a distillation zone which may be a fractional distillation column, or a series of columns, effective to separate the volatile components from the product acid and to separate the product acid from the less volatile catalyst components of the reaction mixture. The boiling points of the volatile components are sufficiently far apart that their separation by conventional distillation presents no particular problem. Likewise, the higher-boiling organic components can be readily distilled away from the metal catalyst components. The thus-recovered co-catalyst, including the iodide component, can then be combined with fresh amounts of alcohol and carbon monoxide and reacted to produce additional quantities of carboxylic acid.

Although not necessary, the process can be carried out in the presence of a solvent or diluent. When the alcohol has a relatively low boiling point, as in the case of methanol, the presence of a higher-boiling solvent or diluent, preferably the product acid itself, e.g., acetic acid in the case of methanol, or the corresponding ester, e.g., methyl acetate, again in the case of methanol, will make it possible to employ more moderate total pressures. Alternatively, the solvent or diluent may be any organic solvent which is inert in the environment of the process such as hydrocarbons, e.g., octane, benzene, toluene, xylene and tetralin, or halogenated hycrocarbons such as the chlorobenzenes, e.g., trichlorobenzene, or carboxylic acids, or esters such as cellosolve acetate, and the like. Mixtures of solvents can also be used, such as mixtures of methyl acetate and acetic acid. The carboxylic acid, when used, should preferably correspond to the acid being produced since, as indicated above, the preferred solvent is one that is indigenous to the system, e.g., acetic acid and/or methyl acetate in the case of methanol carbonylation. A solvent or diluent, when not the product itself, is suitably selected which has a boiling point sufficiently different from the desired product in the reaction mixture so that it can be readily separated, as will be apparent to persons skilled in the art.

The carbon monoxide is preferably employed in substantially pure form, as available commercially, but inert diluents such as carbon dioxide, nitrogen, methane, and noble gases can be present if desired. The presence of inert diluents does not affect the carbonylation reaction but their presence makes it necessary to increase the total pressure in order to maintain the desired CO partial pressure. The presence of minor amounts of water such as may be found in the commercial forms of the reactants is, however, entirely acceptable. Hydrogen which may be present as an impurity is not objectionable and even may tend to stabilize the catalyst. Indeed, in order to obtain low CO partial pressures the CO fed may be diluted with hydrogen or any inert gas such as those mentioned above. It has been surprisingly found that the presence of hydrogen does not lead to the formation of reduction products. The diluent gas, e.g., hydrogen, may generally be used in amount up to about 95%, if desired.

The co-catalyst components can be employed in any convenient form. For example, the nickel and the molybdenum or tungsten can be the metals themselves in finely-divided form, or a compound, both organic or inorganic, which is effective to introduce these co-catalyst components into the reaction system. Thus, typical compounds include the carbonate, oxide, hydroxide, bromide, iodide, chloride, oxyhalide, hydride, lower alkoxide (methoxide), phenoxide, or Mo, W or Ni carboxylates wherein the carboxylate ion is derived from an alkanoic acid of 1 to 20 carbon atoms such as acetates, butyrates, decanoates, laurates, benzoates, and the like. Similarly, complexes of these co-catalyst components can be employed, e.g., carbonyls and metal alkyls as well as chelates, association compounds and enol salts. Examples of other complexes include bis-(triphenylphosphine) nickel dicarbonyl, tricyclopentadienyl trinickel dicarbonyl, tetrakis (triphenylphosphite) nickel, and corresponding complexes of the other components, such as molybdenum hexacarbonyl and tungsten hexacarbonyl. Particularly preferred are the elemental forms, compounds which are halides, especially iodides, and organic salts, e.g., salts of the monocarboxylic acid corresponding to the acid being produced.

The alkali metal component, e.g., a metal of Group IA of the Periodic Table such as lithium, potassium, sodium, and cesium, is suitably employed as a compound, especially a salt, and most preferably a halide, e.g., an iodide. The preferred alkali metal is lithium. The alkali metal component can, however, also be employed as the hydroxide, carboxylate, alkoxide or in the form of other convenient compounds such as are referred to above in connection with the other co-catalyst components, and typical alkali metal components are illustrated by sodium iodide, potassium iodide, cesium iodide, lithium iodide, lithium bromide, lithium chloride, lithium acetate, and lithium hydroxide.

It will be understood that the above-mentioned compounds and complexes are merely illustrative of suitable forms of the several co-catalyst components and are not intended to be limiting.

The specified co-catalyst components employed may contain impurities normally associated with the commercially available metal or metal compounds and need not be purified further.

The amount of each co-catalyst component employed is in no way critical and is not a parameter of the process of the invention and can vary over a wide range. As is well known to persons skilled in the art, the amount of catalyst used is that which will provide the desired suitable and reasonable reaction rate since reaction rate is influenced by the amount of catalyst. However, essentially any amount of catalyst will facilitate the basic reaction and can be considered a catalytically-effective quantity. Typically, however, each catalyst component is employed in the amount of 1 millimol to 1 mol per liter or reaction mixture, preferably 15 millimoles to 500 millimoles per liter and most preferably 15 millimoles to 150 millimoles per liter.

The ratio of nickel to the molybdenum, or tungsten co-catalyst component can vary. Typically, it is one mol of the nickel component per 0.01 to 100 mols of the second co-catalyst component, i.e., the molybdenum, or tungsten, component, preferably the nickel component is used in the amount of 1 mol per 0.1 to 20 mols, most preferably 1 mol per 1 to 10 mols of the second co-catalyst component. Similarly, the ratio of nickel to the alkali metal component can vary e.g. one mol of nickel per 1 to 1000 mols of alkali metal component, preferably 10 to 100 and most preferably 20 to 50.

The amount of iodide component may also vary widely but, in general, it should be present in an amount of at least 0.1 mol (expressed as I) per mol of nickel. Typically, there are used 1 to 100 mols of the iodide per mol of nickel, preferably 2 to 50 mols per mol. Ordinarily, more than 200 mols of iodide per mol of nickel are not used. It will be understood, however, that the iodide component does not have to be added to the system as a hydrocarbyl iodide but may be supplied as another organic iodide or as the hydroiodide or other inorganic iodide, e.g., a salt, such as the alkali metal or other metal salt, or even as elemental iodine. The foregoing also applies to a bromide component when the iodide is replaced with a bromide.

As previously mentioned, the catalyst system of this invention comprises an iodide component and a molybdenum-nickel-alkali metal or tungsten-nickel-alkali metal co-catalyst component. The catalyst system of this invention permits the production of carboxylic acids in high yields in short reaction times without the use of Group VIII noble metals and the presence of the alkali metal component together with the molybdenum or tungsten component makes possible good results with relatively small amounts of co-catalyst components and reduced quantities of nickel in comparison with prior art processes involving a nickel-containing catalyst.

A particular embodiment of the catalyst comprising the molybdenum-nickel-alkali metal or tungsten-nickel-alkali metal co-catalyst component and the iodide component can be represented by the following formula: X:T:Z:Q, wherein X is molybdenum or tungsten, T is nickel, X and T being in zero valent form or in the form of a halide, an oxide, a carboxylate of 1 to 20 carbon atoms, a carbonyl or an hydride; Z is an iodide source which is hydrogen iodide, iodine, an alkyl iodide wherein the alkyl group contains 1 to 20 carbon atoms or an alkali metal iodide, and Q is the alkali metal component. The preferred alkali metal is lithium as previously indicated, and being in the form of an iodide or a bromide or a carboxylate as defined for X and T, the molar ratio of X to T being 0.1–10:1, the molar ratio of X+T to Q being 0.1–10:1, and the molar ratio of Z to X+T being 0.01–0.1:1. The iodide component can be replaced with a bromide.

It will be apparent that the above-described reaction lends itself readily to continuous operation in which the reactants and catalyst are continuously supplied to the appropriate reaction zone and the reaction mixture continuously distilled to separate the volatile organic constituents and to provide a net product consisting essentially of carboxylic acid with the other organic components being recycled and, in a liquid-phase reaction a residual catalyst containing fraction also being recycled.

It will also be apparent that the catalytic reaction involved in the process of the invention can be carried out in the vapor phase, if desired, by appropriate control of the total pressure in relation to the temperature so that the reactants are in vapor form when in contact with the catalyst. In the case of vapor-phase operation, and in the case of liquid-phase operation, if desired, catalyst components may be supported i.e., they may be dispersed on a carrier of conventional type such as alumina, silica, silicon carbide, zirconia, carbon, bauxite, attapulgus clay, and the like. The catalyst components can be applied to the carriers in conventional manner, e.g., by impregnation of the carrier with a solution of the catalyst component. Concentrations upon the carrier may vary widely, e.g., 0.01 weight percent to 10 weight percent, or higher. Typical operating conditions for vapor-phase operation are a temperature of 100° to 350° C., preferably 150° to 275° C. and most perferably 175° to 255° C., a pressure of 1 to 5,000 p.s.i.a., preferably 59 to 1,500 p.s.i.a. and most preferably 150 to 500 p.s.i.a., with space velocities of 50 to 10,000 hr.$^{-1}$, preferably 200 to 6,000 hr.$^{-1}$ and most preferably 500 to 4,000 hr.$^{-1}$ (STP). In the case of a supported catalyst the iodide component is included with the reactants and not on the support.

The following examples will serve to provide a fuller understanding of the invention, but it is to be understood that they are given for illustrative purposes only, and are not to be construed as limitative of the invention. In the examples, all parts are by weight and percentages are on a molar basis, unless otherwise indicated.

EXAMPLE 1

A one-liter Parr autoclave was charged with 150.1 parts of methanol, 150.1 parts of acetic acid as solvent, 7.5 parts of nickel iodide, 15 parts of molybdenum carbonyl, 60.8 parts of lithium iodide and 100.4 parts of methyl iodide. The reactor was flushed three times with 50 psig of carbon monoxide and then pressured with 70 psig of hydrogen and 530 psig of carbon monoxide. Then the reactor was heated to 200° C. and maintained at this temperature for 1 hour and 22 minutes, during which time the pressure was maintained at 1200 psig by charging carbon monoxide as required. The contents of the reactor were then removed and analyzed by gas chromatography. Analysis showed the reaction mixture to contain 71 wt. % acetic acid, the remainder being methyl iodide and the catalyst components. This reaction produced acetic acid with a yield based on methanol of 100% and at a rate of 12.3 mols per liter per hour.

EXAMPLE 2

The autoclave described in Example 1 was charged with 250 parts of methyl acetate as solvent, 50.8 parts of methyl iodide, 100.4 parts of methanol, 7.5 parts of nickel iodide, 15.6 parts of molybdenum carbonyl, and 60.2 parts of lithium iodide. The reactor was flushed three times with 50 psig of carbon monoxide and then pressured with 600 psig of carbon monoxide. Then the reactor was heated to 200° C. and maintained at this temperature for 1 hour, during which time the pressure was maintained at 1000 psig by charging carbon monoxide as required. The contents of the reactor were then removed and analyzed by gas chromatography. Analysis showed the reaction mixture to contain 41 wt. % of acetic acid, the remainder being primarily methyl iodide and the catalyst components. This reaction produced acetic acid with a yield based on methanol of 95% and at a rate of 9.32 mols per liter per hour.

EXAMPLE 3

The reactor described in Example 1 was charged with 150.9 parts of methyl acetate as solvent, 150.4 parts of methyl iodide, 100.4 parts of methanol, 7.5 parts of nickel iodide, 15.1 parts of tungsten carbonyl, and 60.3 parts of lithium iodide. The reactor was flushed three times with 50 psig of carbon monoxide and then presured with 70 psig of hydrogen and 530 psig of carbon monoxide. The reaction was then carried out as described in Example 2. Analysis showed the reaction mixture to contain 41.5 wt. % acetic acid, the remainder being primarily methyl iodide and the catalyst components. This reaction produced acetic acid with a yield based on methanol of 96.4 % and at the rate of 9.49 mols per liter per hour.

EXAMPLE 4

A one-liter Parr autoclave was charged with 250 parts of methyl acetate, 150.1 parts of methyl iodide, 50.3 parts of water, 7.6 parts of nickel iodide, 15 parts of molybdenum carbonyl, and 60 parts of lithium iodide. The reactor was flushed three times with 50 psig of carbon monoxide and then pressured with 70 psig of hydrogen and 530 psig of carbon monoxide. Then the reactor was heated to 200° C. and maintained at this temperature for 32 minutes, during which time the pressure was maintained at 1200 psig by charging carbon monoxide as required. The contents of the reactor were then removed and analyzed by gas chromotography. Analysis showed the reaction mixture to contain 55 wt. % acetic acid and 2.6 % acetic anhydride, the remainder being essentially methyl iodide and the catalyst components. This reaction produced acetic acid with a yield based on methyl acetate and water of 100 % and at the rate of 18 mols per liter per hour.

EXAMPLE 5

A Parr autoclave described in Example 1 was charged with 250.2 parts of methyl acetate, 50.3 parts of methyl iodide, 70.9 parts of water, 7.5 parts of nickel iodide, 15.4 parts of chromium carbonyl, and 60.5 parts of lithium iodide. The reactor was flushed three times with 50 psig of carbon monoxide and then pressured with 70 psig of hydrogen and 530 psig of carbon monoxide. Then the reactor was heated to 200° C. and maintained at this temperature for 1 hour during which time the pressure was maintained at 1000 psig by charging carbon monoxide as required. G.C. analysis showed the reaction mixture to contain 74 wt. % of acetic acid, the remainder being essentially methyl iodide and the catalyst components. This reaction produced acetic acid with a yield based on methyl acetate of 100% and at a rate of 10 mols per liter per hour.

EXAMPLE 6

The previously-described autoclave was charged with 250 parts of methyl acetate, 50.2 parts of methyl iodide, 70 parts of water, 7.5 parts of nickel iodide, 15 parts of molybdenum carbonyl, and 60.1 parts of lithium iodide. The reactor was flushed three times with 50 psig of carbon monoxide and then pressured with 600 psig of carbon monoxide. Then the reactor was heated to 200° C. and maintained at this temperature for 2 hours, during which time the pressure was maintained at 600 psig by charging carbon monoxide as required. G.C. analysis showed the reaction mixture to contain 9.8 of methyl acetate and 56.7 wt. % of acetic acid, the remainder being methyl iodide and the catalyst components. This reaction produced acetic acid with a yield based on methyl acetate of 74 % and at the rate of 4.99 mols per liter per hour.

EXAMPLE 7

A one-liter Parr autoclave was charged with 250.2 parts of methyl acetate, 50.9 parts of methyl iodide, 100.5 parts of water, 7.5 parts of nickel iodide, 15.6 parts of molybdenum carbonyl, and 90.4 parts of cesium iodide. The procedure described in Example 4 was then followed except that the reaction was carried out at 1100 psig for 2 hours. G.C. analysis showed the reaction mixture to contain 1.358 wt. % of methyl acetate, 62.4 wt. % of acetic acid, the remainder being primarily methyl iodide and the catalyst components. This reaction produced acetic acid with a yield based on methyl acetate of 93.6 % at the rate of 8.4 mols per liter per hour.

EXAMPLE 8

The Parr autoclave of the previous examples was charged with 250.9 parts of methyl acetate, 50.8 parts of methyl iodide, 90.1 parts of water, 7.6 parts of nickel iodide, 15 parts of molybdenum carbonyl, and 60.2 parts of lithium iodide. The procedure described in Example 6 was followed except that the pressure was maintained at 1000 psig for 1 hour and 7 minutes. G.C. analysis showed the reaction mixture to contain 0.42 % of methyl acetate and 67.4 wt. % of acetic acid, the remainder being essentially methyl iodide and the catalyst components. This reaction produced acetic acid with a yield based on methyl acetate of 94.9 at the rate of 8.7 mols per liter per hour.

EXAMPLE 9

Example 1 was repeated but at 180° C. It was found that the yield and reaction rate fell to a considerable extent, indicating the need for a higher temperature to obtain the best results with the catalyst.

I claim:

1. A process for the preparation of a carboxylic acid which comprises reacting a hydrocarbyl alcohol of the formula ROH wherein R is alkyl of 1–11 carbon atoms or phenyl or benzyl with carbon monoxide in the presence of a molybdenum-nickel-alkali metal or a tungstennickel-alkali metal co-catalyst component and in the presence of an iodide or bromide.

2. A process as defined in claim 1, wherein the co-catalyst component is molybdenum-nickel-alkali metal.

3. A process as defined in claim 1, wherein the alkali metal is lithium.

4. A process as defined in claim 3, wherein the co-catalyst component is molybdenum-nickel-lithium.

* * * * *